US012564586B2

(12) United States Patent
Porreca et al.

(10) Patent No.: US 12,564,586 B2
(45) Date of Patent: Mar. 3, 2026

(54) KAPPA OPIOD RECEPTOR ANTAGONISTS FOR TREATING PAIN-RELATED SLEEP DISORDERS

(71) Applicant: ARIZONA BOARD OF REGENTS ON BEHALF OF THE UNIVERSITY OF ARIZONA, Tucson, AZ (US)

(72) Inventors: Frank Porreca, Tucson, AZ (US); Hisakatsu Ito, Tucson, AZ (US); Edita Navratilova, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 590 days.

(21) Appl. No.: 17/906,541

(22) PCT Filed: Apr. 9, 2021

(86) PCT No.: PCT/US2021/026687
§ 371 (c)(1),
(2) Date: Sep. 16, 2022

(87) PCT Pub. No.: WO2021/207678
PCT Pub. Date: Oct. 14, 2021

(65) Prior Publication Data

US 2023/0146937 A1 May 11, 2023

Related U.S. Application Data

(60) Provisional application No. 63/007,686, filed on Apr. 9, 2020.

(51) Int. Cl.

| | |
|---|---|
| ***A61K 31/4709*** | (2006.01) |
| ***A61K 31/40*** | (2006.01) |
| ***A61K 31/485*** | (2006.01) |
| ***A61P 25/04*** | (2006.01) |
| ***A61P 25/20*** | (2006.01) |

(52) U.S. Cl.
CPC ............ *A61K 31/485* (2013.01); *A61K 31/40* (2013.01); *A61K 31/4709* (2013.01); *A61P 25/04* (2018.01); *A61P 25/20* (2018.01)

(58) Field of Classification Search
CPC ....... A61K 31/4709; A61P 25/00; A61P 25/04
USPC .................................................. 514/314, 313
See application file for complete search history.

(56) References Cited

U.S. PATENT DOCUMENTS 9,512,105 B2 * 12/2016 Carroll ................. C07D 241/04
9,540,375 B2 * 1/2017 Aube ................. A61K 31/4439

OTHER PUBLICATIONS

Kumagai, H et al.: Efficacy and safety of a novel k-agonist for managing intractable pruritus in dialysis patients. Am. Journal of Nephrol. and Endocrin., vol. 36, pp. 175-183, 2012.*

* cited by examiner

*Primary Examiner* — Charanjit Aulakh
(74) *Attorney, Agent, or Firm* — NGUYEN TARBET IP LAW

(57) ABSTRACT

Chronic pain patients complain about sleep disturbance with a high probability, while sleep loss increases pain in chronic pain patients. Sleep problems and pain promote a vicious spiral, suggesting a need for simultaneous treatment of both. The present invention provides a method to treat pain-related sleep disorders through distribution of a therapeutic amount of a KOR antagonist. The use of KOR antagonist could be a novel therapeutic agent for sleep disturbance in chronic pain patients. Additionally, KOR antagonists could be used to improve sleep in other conditions, such as depression or general anxiety disorder, where KOR signaling is induced.

10 Claims, 13 Drawing Sheets

Head-mount
Recovery
Baseline
Minipump
Recovery
Test day1 – day5
EEG record for 24hrs % of sleep
Day1
Light
Dark
Clock time
Day3
Day5
Vehicle
U69,593

Light phase
Dark phase
% of sleep
Non-REM sleep time (hours)
REM sleep time (hours)
Baseline
day1
day2
day3
day4
day5

Non-REM sleep

REM sleep

KAPPA OPIOD RECEPTOR ANTAGONISTS FOR TREATING PAIN-RELATED SLEEP DISORDERS

CROSS-REFERENCES TO RELATED APPLICATIONS

This application claims benefit of U.S. Provisional Application No. 63/007,686 filed Apr. 9, 2020, the specification of which is incorporated herein in their entirety by reference.

STATEMENT REGARDING FEDERALLY SPONSORED RESEARCH OR DEVELOPMENT

This invention was made with government support under Grant No. R01 NS106902 and P01 DA041307 awarded by National Institutes of Health. The government has certain rights in the invention.

FIELD OF THE INVENTION

The present invention relates to a method of treating secondary sleep disturbance induced by chronic pain or aging, more particularly to a method that blocks kappa opioid receptor (KOR) signaling through the use of a therapeutic amount of a KOR antagonist.

BACKGROUND OF THE INVENTION

Sleep disturbances and chronic pain have a significant bidirectional relationship. Previous clinical research reported that most (i.e., 50-80%) but not all patients with chronic pain complain about poor sleep. The relative hazard ratio of sleep disturbances in chronic pain patients is two to five times higher as compared with healthy individuals. The prevalence of severe sleep problems is incrementally increased with pain severity, so the sleep complaints may be a good biomarker of severity of chronic pain. On the other hand, people fulfilling the criteria for insomnia disorder have a high rate of comorbidity of chronic pain and show higher sensitivity to a transient painful (i.e., nociceptive) stimulation rather than individuals without insomnia. Even acute sleep-deprivation of only one day also amplifies pain reactivity to external stimuli. In an animal-based sleep deprivation study, a dose-response relationship was observed between the time of sleep disturbance and the decrease in pain threshold to a stimulus.

Sleep problems are a potential cause of mental and physical health problems independent of pain. Sleep disturbance increases the risk for the mental disorders such as depression, anxiety, and substance misuse, and could be significant risk of obesity, diabetes, hypertension and critical vascular disease including stroke and myocardial infarction. The patient's quality of life is definitely reduced by sleep disturbances that can occur for many reasons as a result of, or independently of, pain. If sleep disturbance is a result of chronic pain, both sleep and pain should ideally be treated in a clinical situation. Currently, treatments that improve sleep do not improve chronic pain while some treatments that improve chronic pain can disrupt sleep even further. Usually, treatment of pain typically ignores the treatment of sleep disruption and vice-versa. Treatments that improve both are lacking in the market.

BRIEF SUMMARY OF THE INVENTION

It is an objective of the present invention to provide a treatment for secondary sleep disturbance induced by chronic pain or age in a subject in need of such treatment through the blocking of an opioid receptor signaling pathway, as specified in the independent claims. Embodiments of the invention are given in the dependent claims. Embodiments of the present invention can be freely combined with each other if they are not mutually exclusive.

Negative consequences associated with chronic pain and sleep deprivation result from primary biological mechanisms that are not well understood. However, chronic pain is known to produce hyper-activation of neural circuits in the brain resulting from engagement of the kappa opioid receptor (KOR) to elicit a prolonged maladaptive state of homeostatic dysregulation. Dynorphin, an endogenous neurotransmitter that activates KOR, has been shown to be increased in chronic pain.

Dynorphin/Kappa opioid receptor (KOR) signaling in brain circuits plays a central role in pain responses. In animal models, antagonism of KOR signaling blocks the aversive (i.e., affective), but not sensory, components of pain. It is hypothesized in the present invention that the aversive qualities of chronic pain are mediated through dynorphin engagement of the KOR in specific neural circuits in the brain that do not alter sensory components of pain. Here it is shown that KOR may be a new therapeutic target for improvement of sleep in brain circuits disrupted by chronic pain and improving the aversive qualities of pain, independently of sensory aspects of pain, will improve pain-related sleep disturbances.

Disruption of sleep is a pertinent problem to patients who struggle with chronic pain. There is also the problem of a disruption of sleep, or lack of sleep in general, increasing pain further for chronic pain patients. Activation of kappa opioid receptor (KOR) signaling, especially in the paraventricular nucleus of the hypothalamus plays an important role in disrupting sleep. However, activation of the KOR in the paraventricular nucleus of the hypothalamus does not promote pain.

In some aspects, the present invention may feature a method of treating sleep disruption induced by chronic pain in a subject in need of such treatment. According to one embodiment, the method may comprise administering to the subject a therapeutically effective amount of a composition comprising a kappa opioid receptor (KOR) antagonist. The KOR antagonist may be capable of treating the sleep disruption induced by chronic pain such that clinical improvement is observed. Examples of KOR antagonists include, but are not limited to nor-BNI, CYM53093/BTRX-331540, and CERC-501. In other aspects, the present invention may also feature a KOR antagonist composition for use in a method for treating sleeping disturbance induced by chronic pain.

In some embodiments, the present invention may further feature a method of treating a condition that causes an increase in kappa opioid receptor (KOR) signaling in a subject in need of such treatment. The method may comprise administering a therapeutic amount of an opioid receptor antagonist.

In other embodiments, the present invention may feature a method of treating age related sleep disruption. According to one embodiment, the method may comprise administering to the subject a therapeutically effective amount of a composition comprising a kappa opioid receptor (KOR) antagonist. The KOR antagonist may be capable of treating the sleep disruption induced by aging such that clinical improvement is observed.

One of the unique and inventive technical features of the present invention is the administering of a KOR antagonist as a therapeutic treatment for secondary sleep disturbance that has already been induced by chronic pain. Administering a KOR antagonist (such as nor-BNI or CYM53093) improved several important components of pain-related sleep disturbance including sleep time loss, fragmentation of sleep, and daytime sleepiness in a mouse model of chronic neuropathic pain. Without wishing to limit the invention to any theory or mechanism, it is believed that the technical feature of the present invention advantageously provides for treatment that can be used long term and also in combination with other drugs to help treat sleep disturbance due to chronic pain. None of the presently known prior references or work has the unique inventive technical feature of the present invention.

Furthermore, the prior references teach away from the present invention for several reasons. First, current treatments are not aimed at patients with sleep problems as well as with chronic pain and are designed to treat either sleep or pain rather than both. Second, current treatments for sleep problems are not recommended for long term use due to likelihood of becoming habit forming or addictive and are not recommended for use in conjunction with other medications. Third, prior art teaches that kappa opioid agonists produce pain relief as demonstrated in clinical trials with enadoline. However, the present invention is based on the improvement of sleep from KOR antagonists that do not affect the sensory qualities of pain but rather modulate the aversiveness of pain and improve sleep in models of chronic pain. These effects of KOR antagonists may occur in the same, or in different neural circuits in the brain.

Furthermore, the inventive technical features of the present invention contributed to a surprising result. For example, it was found that KOR agonists or chemogenetic activation of KOR expressing cells in the hypothalamus disrupted sleep in uninjured mice without producing pain suggesting that the KOR circuits mediating sleep and pain may exist in parallel. The effects of the KOR antagonist may therefore result from independent improvement in sleep and improvement in pain in different brain regions. Additionally, it was surprising that KOR antagonists improved pain in the chronic neuropathic pain model as sensory thresholds were not altered in the mice. An additional surprising outcome is that the KOR antagonist could be given after chronic pain was established to improve already disrupted sleep. It was a surprise from the present study that KOR antagonists did not improve REM sleep in animals with chronic pain and in fact, disrupted REM sleep even in animals without pain. This was consistent with the lack of KOR agonist effects on REM sleep in uninjured animals. These outcomes were opposite from the teaching of the work of Carlezon and colleagues who found that pretreatment with KOR antagonists before social defeat stress (a) improved REM sleep in their animals and (b) that social defeat stress did not induce pain.

Another unique and inventive technical feature of the present invention is the administering of a KOR antagonist as a therapeutic treatment for age-related sleep disturbance. Without wishing to limit the invention to any theory or mechanism, it is believed that the technical feature of the present invention advantageously provides for treatment that normalizes sleep and prevents cognitive impairment.

Furthermore, the prior references teach away from the present invention. For example, other methods of treating age-related sleep disorders such as drugs that modulate GABA channels (e.g., Ambien or alcohol) that produce unnatural sleep.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIGS. 1A-1H shows KOR agonist, U69,593, attenuates sleep in uninjured mice. FIG. 1A shows how the experiment was set up to analyze Electroencephalogram/Electromyogram (EEG/EMG) to evaluate the sleep condition for 5 days after one day surgical recovery from osmotic-pump implantation. FIG. 1B demonstrates that U69,593 (KOR agonist) reduced sleep time generally as compared to vehicle (indicated with a circle) during both light and dark phases. FIGS. 1C-1E show U69,593 reduced the amount of sleep time during both light and dark phases from test day 1 to 5. U69,593 reduced non-REM sleep, but not REM sleep. FIG. 1F shows that at test day 5, U69,593 injected mice became unable to keep awake during the dark (active) phase. This is reminiscent of daytime sleepiness in patients with sleep disorders. FIGS. 1G-1H show U69,593 fragmented non-REM sleep through all periods and decreased the power density of slow waves in δ waves.

FIGS. 2A-2I shows that the KOR antagonist improves sleep distribution in a chronic pain model. FIG. 2A shows how the experiment was set up to analyze sleep disruption in a preclinical model of chronic pain induced by partial sciatic nerve ligation (PSNL). FIGS. 2B-2C show that the delivery of nor-BNI (KOR antagonist) normalized the deficit of sleep time of the partial sciatic nerve ligation (PSNL) group to the same as baseline measured before PSNL surgery but had no effect in the sham surgery group. FIG. 2D-2F looked at the percentage of total sleep, non-REM sleep and REM sleep in PSNL or sham surgery mice with or without nor-BNI. FIG. 2G shows nor-BNI improved the inability to stay awake during the dark (active) time of the day. FIG. 2H-2I shows nor-BNI improved sleep fragmentation in PSNL during non-REM sleep but did not change the power spectrum.

FIGS. 3A-3H show continuous administration of short acting KOR antagonists improves sleep condition in chronic pain. FIG. 3A shows how the experiment was set up to evaluate the effects of continuous delivery of short-acting KOR antagonist (CYM53093) on sleep in a chronic pain model (PSNL). FIGS. 3B-3C show CYM53093 normalized the reduction of sleep time up until day 4. FIGS. 3D-3G show CYM53093 improved non-REM sleep, wakefulness during the first part of the dark phase, normalized fragmentation of non-REM sleep but did not improve REM sleep. FIG. 3H shows no change in the power density of CYM53093 groups.

FIGS. 4A-4H show stimulation of Gi signaling in KOR expressing cells in the hypothalamus disrupts sleep. FIG. 4A shows how the experiment was set up to evaluate KOR signaling in the hypothalamus. FIGS. 4B-4C show sleep time was reduced for mice with hM4Di (an artificial Gi coupled receptor which mimics KOR signaling). FIGS. 4D-4G show hM4Di activation reduced non-REM sleep time and fragmented the mean duration of non-REM sleep but had no effect on REM sleep and on the duration of the wake stage. FIG. 4H shows hM4Di activation did not change power of 6 wave compared with vehicle.

DETAILED DESCRIPTION OF THE INVENTION

Figures 1A, 1B, 1C, 1D, 1E:
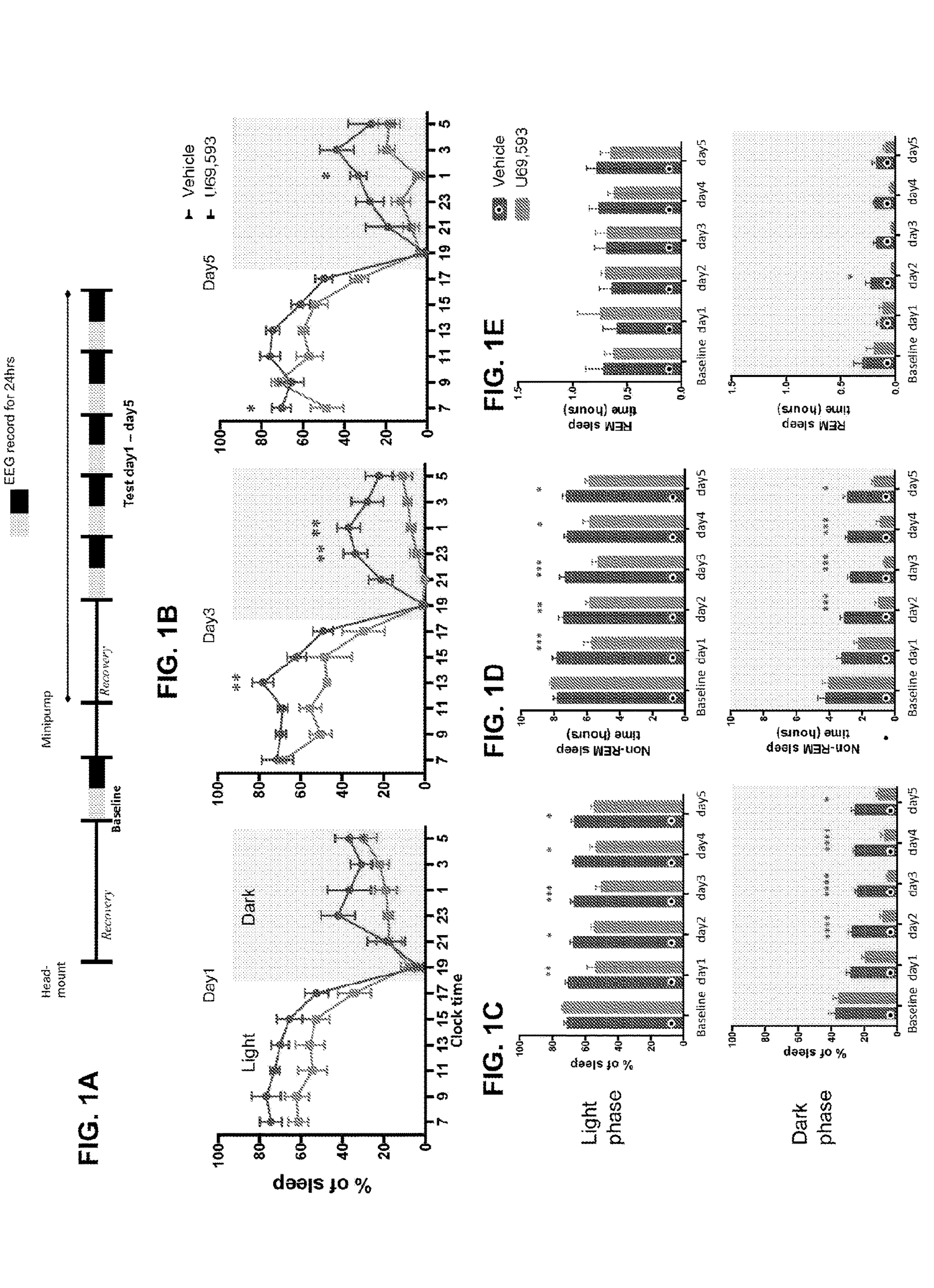
Figure 1F:
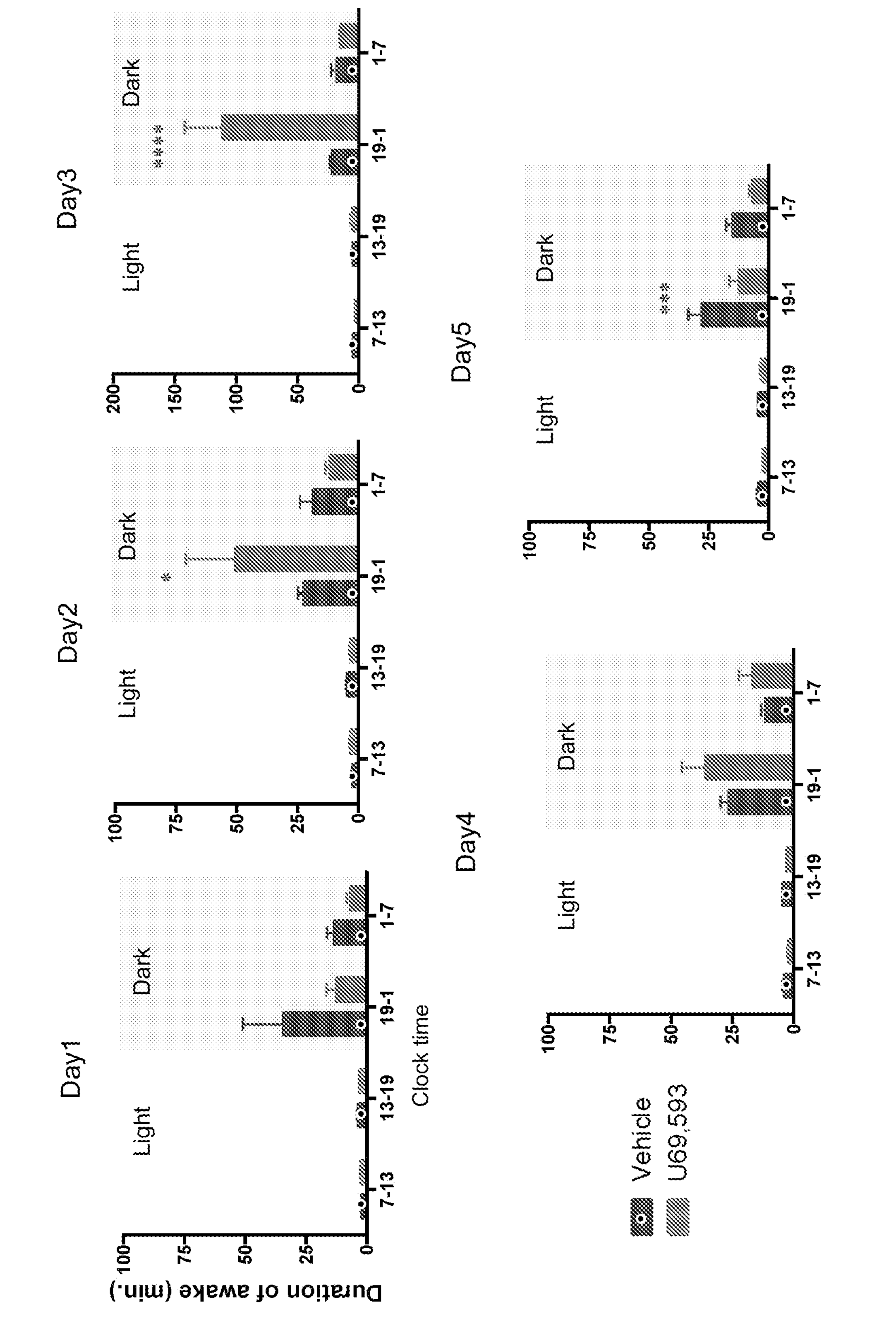
Figure 1G:
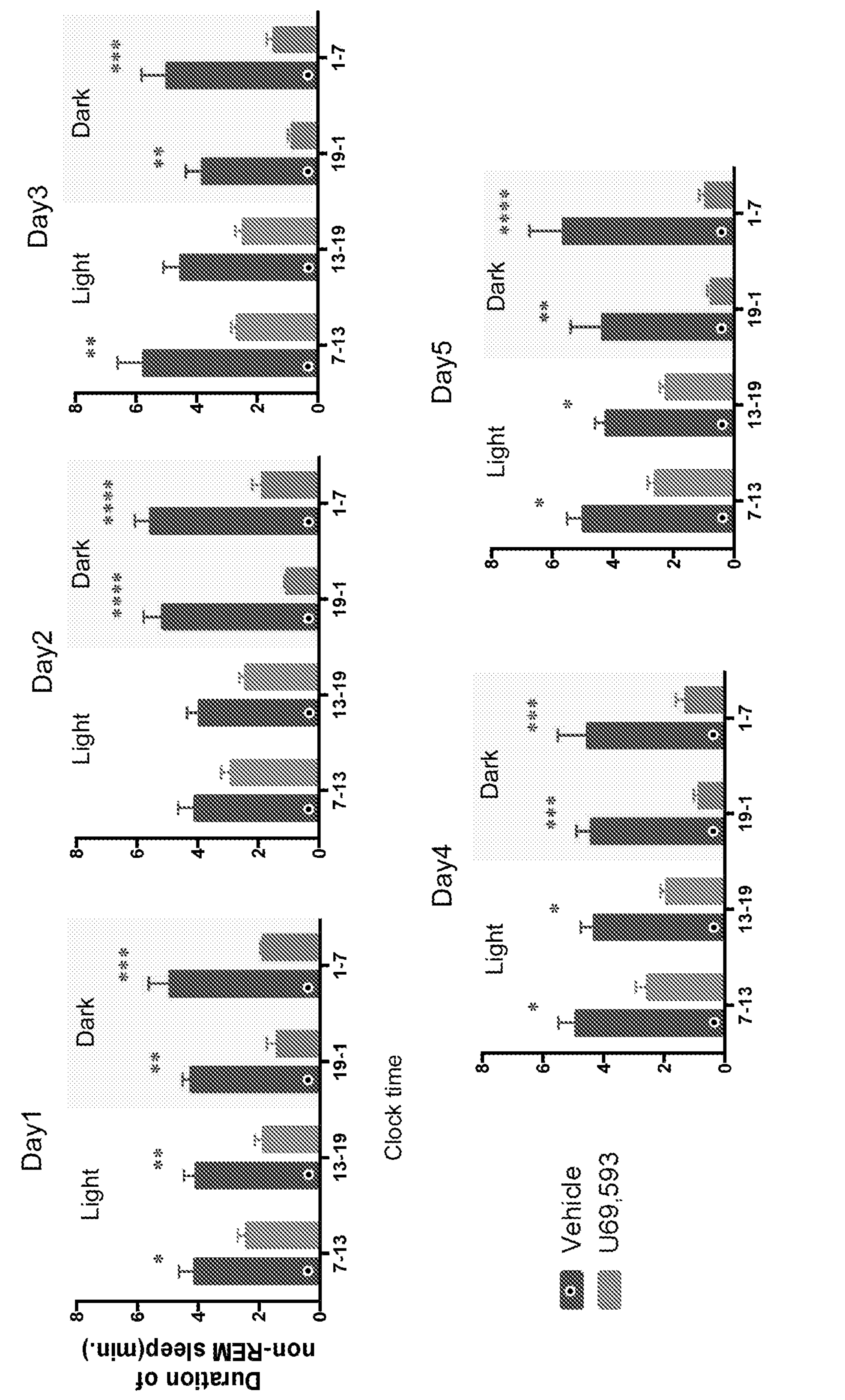
Figure 1H:
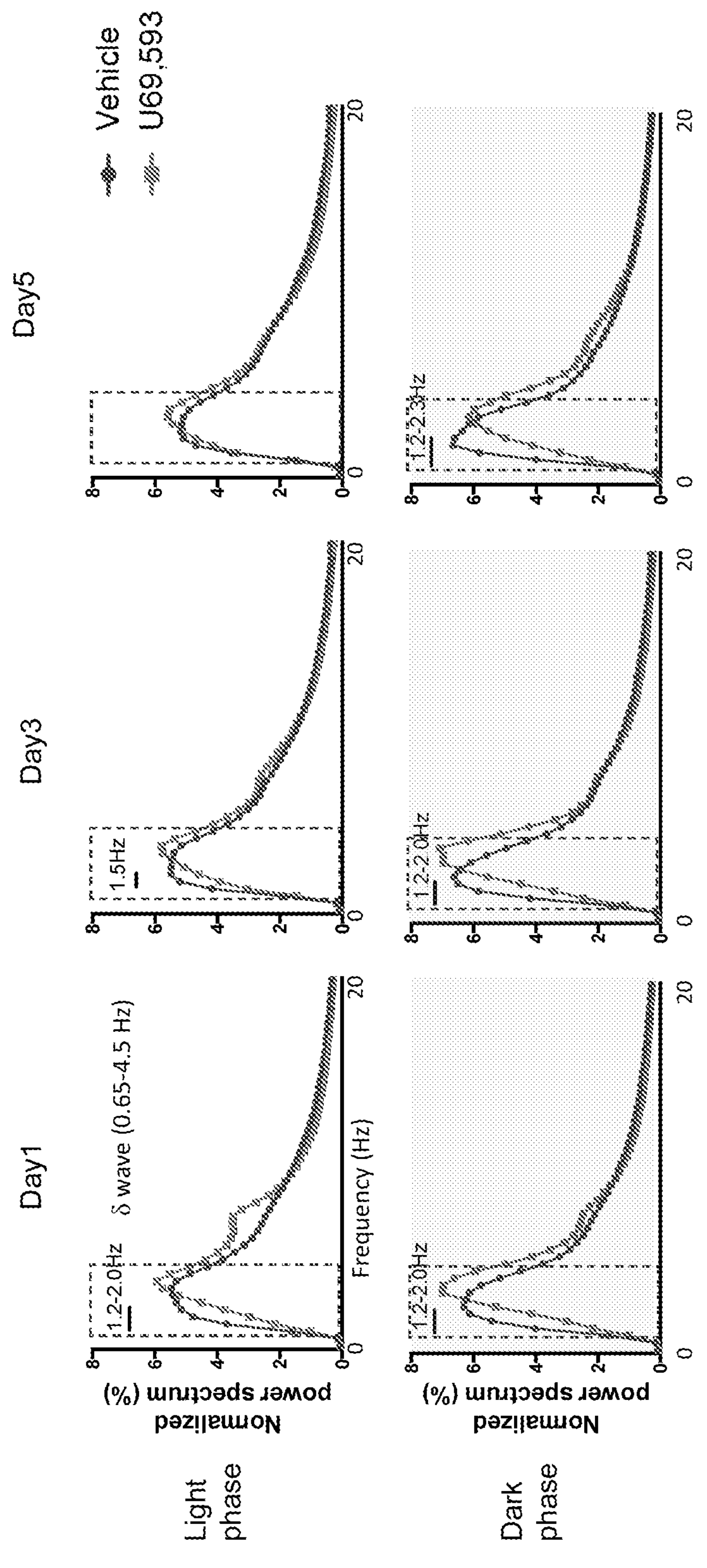

Before the present compounds, compositions, and/or methods are disclosed and described, it is to be understood that this invention is not limited to specific synthetic methods or to specific compositions, as such may, of course, vary. It is also to be understood that the terminology used herein is for the purpose of describing particular embodiments only and is not intended to be limiting.

According to one embodiment, the present invention may feature a method of treating a secondary sleep disturbance induced by chronic pain in a subject in need of such treatment. According to one embodiment the method comprises administering a therapeutic amount of an opioid antagonist. The method may be capable of treating sleep disturbance induced by chronic pain such that clinical improvements are observed. In some embodiments, the opioid receptor antagonist is effective at treating both the secondary sleep disturbance and the chronic pain. In other embodiments, the opioid receptor antagonist is specific for a kappa opioid receptor. In further embodiments, the treatment may be used in combination with other treatments.

The present invention may also feature a method of treating a secondary sleep disturbance induced by chronic pain in a subject in need of such treatment. In some embodiments, the method comprises administering a therapeutic amount of an opioid receptor antagonist, thereby simultaneously treating both the secondary sleep disturbance and the chronic pain. The method may be capable of treating sleep disturbance induced by chronic pain such that clinical improvements are observed. In other embodiments, the opioid receptor antagonist is specific for a kappa opioid receptor. In further embodiments, the treatment may be used in combination with other treatments.

The present invention may further feature a method of treating age-related sleep disturbance in a subject in need of such treatment. In some embodiments, the method comprises administering a therapeutic amount of an opioid receptor antagonist. The method may be capable of treating sleep disturbance induced by age such that clinical improvements are observed. In other embodiments, the opioid receptor antagonist is specific for a kappa opioid receptor. In further embodiments, the treatment may be used in combination with other treatments.

As defined herein, the term "chronic pain" is used in a conventional sense. It is associated with a pain that lasts for more 4-12 weeks and that can last for years.

As defined herein, the term "antagonist" refers to a compound that inhibits a response to an endogenous substance. The antagonist binds to the same receptor as the endogenous compound and prevents or reverses the signal generated by the endogenous agent.

The present invention excludes the use of agonist or partial agonist of the kappa opioid receptor. It is believed that agonist or partial agonists will produce sleep disturbances in a subject which teaches away from the present invention.

As defined herein, the term "sleep disturbance" refers to problems with the quality, timing, and amount of sleep, which result in daytime distress and impairment in functioning. Sleep disturbance may occur along with medical conditions or other mental health conditions, such as depression, anxiety, or cognitive disorders.

As defined herein, the term "age-related sleep disturbance" refers to changes in sleep with aging that may be characterized by increased time to fail asleep, shorter duration of sleep increased awakenings, increased sleep during daytime periods (daytime napping), decreased depth of sleep and other measures commonly related to normal sleep in adults.

As used herein, "clinical improvement" may refer to a noticeable reduction in the symptoms of a disorder, or cessation thereof. In some embodiments, clinical improvement may refer to a reduction in daytime sleepiness, an increase in non-REM sleep, a reduction of sleep fragmentation, or increase of total sleep time.

As used herein, "sleep normalization" or "normalization of sleep" may be determined by measuring time to fall asleep, total time spent asleep, amount of fragmented sleep and amount of daytime sleepiness. In some embodiments, sleep normalization may refer to an increase in total time spent asleep, a decrease in sleep fragmentation, and an increase in the amount of daytime sleepiness.

As used herein, "sleep fragmentation" or "fragmented sleep" may refer to brief arousals that occur during a sleep period. An arousal may refer to an abrupt shift in the electromyogram (EMG) integral and electroencephalographic (EEG) frequency (suggestive of an awake state) which is 3 s or greater in duration and which occurs after at least 10 consecutive seconds of sleep. Additionally, shifts in the EMG integral are important in determining whether a subject is awake or not.

As used herein, "unnatural sleep" may be characterized as sleep that is not restful. In some embodiments, unnatural sleep is associated with impaired cognitive performance the next morning and an increased daytime sleepiness.

According to one embodiment, the present invention may feature a method of treating sleep disruption induced by chronic pain in a subject in need of such treatment. According to one embodiment, the method may comprise administering to the subject a therapeutically effective amount of a composition comprising a kappa opioid receptor (KOR) antagonist in a pharmaceutically acceptable carrier. The composition may be capable of treating the sleep disruption induced by chronic pain such that clinical improvement is observed. Examples of KOR antagonists include, but are not limited to nor-BNI, CYM53093/BTRX-331540, and CERC-501.

According to another embodiment, the present invention may feature a method of treating a condition that causes an increase in kappa opioid receptor (KOR) signalling in a subject in need of such treatment. In some embodiments, the method may comprise administering a therapeutic amount of an opioid receptor antagonist. In some embodiments, the opioid receptor antagonist is specific for a kappa opioid receptor (KOR). In further embodiments, the treatment may be used in combination with other treatments.

Without wishing to limit the present invention to any theory or mechanism, it is believed that an increase in KOR signaling in a subject may be caused by an upregulation of expression of the endogenous KOR ligand, dynorphin.

The present invention may also feature a kappa opioid receptor (KOR) antagonist for use in a method for treating sleep disturbance induced by chronic pain. In some embodiments, the composition simultaneously treats both the secondary sleep disturbance and the chronic pain. Furthermore, the present invention features a kappa opioid receptor (KOR) antagonist for use in a method for treating sleep disturbance induced by aging. In other embodiments, the treatment may be used in combination with other treatments.

In some embodiments, the antagonists are short-acting antagonists. In some embodiments, the antagonists are medium acting antagonists. In another embodiment, the antagonists are long-acting antagonists. Wherein short, medium, and long acting refer to the amount of time (half-life) the compound remains in the body comparatively.

As used herein a "short acting antagonist" may refer to an antagonist with a half-life of about two to four hours. In some embodiments, a short acting antagonist has a half-life of about two hours. In some embodiments, a short acting antagonist has a half-life of about 2.5 hours. In some embodiments, a short acting antagonist has a half-life of about three hours. In some embodiments, a short acting antagonist has a half-life of about 3.5 hours. In some embodiments, a short acting antagonist has a half-life of about four hours.

As used herein a "medium acting antagonist" may refer to an antagonist with a half-life of about 24 to 36 hours. In some embodiments, a medium acting antagonist has a half-life of about 24 hours. In some embodiments, a medium acting antagonist has a half-life of about 26 hours. In some embodiments, a medium acting antagonist has a half-life of about 28 hours. In some embodiments, a medium acting antagonist has a half-life of about 30 hours. In some embodiments, a medium acting antagonist has a half-life of about 32 hours. In some embodiments, a medium acting antagonist has a half-life of about 34 hours. In some embodiments, a medium acting antagonist has a half-life of about 36 hours.

As used herein a "long acting antagonist" may refer to an antagonist with a half-life of 4 days to weeks or months. In some embodiments, a long acting antagonist has a half-life of about 4 days. In some embodiments, a long acting antagonist has a half-life of about 1 week. In some embodiments, a long acting antagonist has a half-life of about 2 weeks. In some embodiments, a long acting antagonist has a half-life of about 3 weeks. In some embodiments, a long acting antagonist has a half-life of about 1 month.

In some embodiments, a long acting antagonist has a half-life of about 2 months. In some embodiments, a long acting antagonist has a half-life of about 4 months. In some embodiments, a long acting antagonist has a half-life of about 6 months.

In some embodiments, the opioid receptor antagonist is nor-BNI. In other embodiments, the opioid receptor antagonist is CYM 53,093/BTRX-331540. In some embodiments, the opioid receptor antagonist is CERC-501. Non-limiting examples of the KOR opioid antagonist may include but is not limited to nor-BNI (Norbinaltorphimine), CYM 53,093/BTRX-331540, CERC-50 (Aticaprant), GNTI (5'-Guanidinonaltrindole), PF-4455242, AZ-MTAB, Arodyn, Zyklophin and Buprenorphine. In some embodiments, any antagonist that acts against or blocks KOR signaling can be used in the present invention to treat a secondary sleep disturbance.

In one embodiment, the subject may be a mammal, such as a human. In another embodiment, the opioid receptor antagonist, e.g. the KOR antagonist, is administered in a dosage of about 0.1 mg to 1000 mg. For example, the dosage may range from about 0.1 mg to about 1000 mg with a preferred range of about 10 mg to about 500 mg. The opioid receptor antagonist may be administered once daily or twice daily; or the opioid receptor antagonist may be administered at least once daily, at least once every other day, or at least once weekly or once monthly or administered for an extended period of time. In further embodiments, the opioid receptor antagonist may be administered orally, intravenously, or transdermally, sublingually or through buccal delivery.

As used herein, an "extended period of time" may refer to a period of time from one day to a year or more. In some embodiments, an extended period of time ranges from a week to one year. In some embodiments, an extended period of time ranges from a week to a year or more. In other embodiments, an extended period of time ranges from one year to two years. In some embodiments, an extended period of time ranges from about two years to three years, or from about three years to five years, or from about five years to ten year. In other embodiments, an extended period of time is over 10 years.

In some preferred embodiments, the opioid receptor antagonist can be administered to a subject who has been diagnosed with a sleep problem induced by any type of chronic pain including, but not limited to, migraine, fibromyalgia, neuropathic pain, chronic inflammation, musculoskeletal pain, dental pain, depression and others. In other embodiments, the opioid receptor antagonist can be administered to a subject who has been diagnosed with a sleep problem induced by aging.

In some embodiments, the opioid receptor antagonist for use may be administered once daily or twice daily. In another embodiment, the opioid receptor antagonist may be administered at least once daily, at least once every other day, or at least once weekly or once monthly or at least for an extended period of time. Further still, the opioid receptor antagonist may be administered intravenously, transdermally, or orally, sublingually or through buccal delivery. In preferred embodiments, the opioid receptor antagonist for use in the treatment resulted in clinical improvement of sleep disturbance induced by chronic pain. For example, clinical improvement may be observed in about 1 to 7 days or about 7 to 14 days.

In some embodiment the opioid receptor antagonist may be administered for an extended period of time. As used herein "an extended period of time" may refer to a period that ranges from a week to years.

In any of the aforementioned embodiments of the present invention, the opioid receptor antagonist may be administered in a dosage of about 0.1 mg to 1000 mg. For example, the dosage may range from about 0.1 mg to 1 mg, 1 mg to 10 mg, 10 mg to 20 mg, 20 mg to 30 mg, 30 mg to 40 mg, 40 mg to 50 mg, 50 mg to 60 mg, 60 mg to 70 mg, 70 mg to 80 mg, 80 mg, to 90 mg, 90 to 100 mg, 100 mg to 200 mg, 200 mg to 300 mg, 300 mg to 400 mg, 400 mg to 500 mg, 500 mg to 600 mg, 600 mg to 700 mg, 700 mg to 800 mg, 800 mg to 900 mg, or 900 mg to 1000 mg.

Without wishing to limit the invention to a particular theory or mechanism, KOR signaling in hypothalamus may disrupt sleep indirectly following dynorphin upregulation in chronic pain and therefore a KOR antagonist that can reduce dynorphin/KOR signaling may be a therapeutic treatment for sleep disturbance induced by chronic pain.

TABLE 1 shows non-limiting examples of KOR antagonists that could be used as a therapeutic treatment for sleep disturbance and chronic pain.

| KOR Antagonist |
| --- |
| 1: nor-BNI |
| 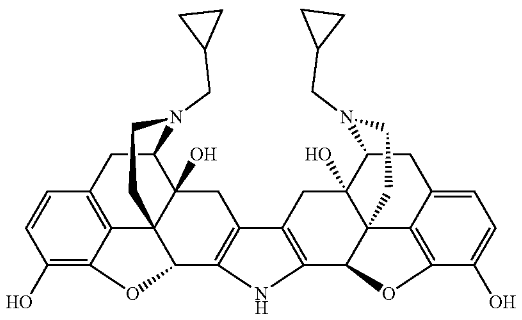 |
| •2HCl |
| 2: CYM 53, 093 |
| 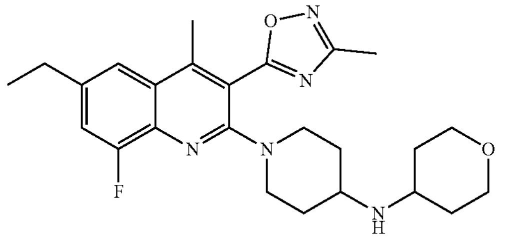 |

Disclosed are the various compounds, solvents, solutions, carriers, and/or components to be used to prepare the disclosed compositions as well as the compositions themselves to be used within the methods disclosed herein. Also disclosed are the various steps, elements, amounts, routes of administration, symptoms, and/or treatments that are used or observed when performing the disclosed methods, as well as the methods themselves. These and other materials, steps, and/or elements are disclosed herein, and it is understood that when combinations, subsets, interactions, groups, etc. of these materials are disclosed, that while specific reference of each various individual and collective combination and permutation of these compounds may not be explicitly disclosed, each is specifically contemplated and described herein.

In some embodiments, the KOR antagonist of the present invention is conjugated to a moiety as to provide a prodrug.

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects.

The terms "administering", and "administration" refer to methods of providing a pharmaceutical preparation to a subject. Such methods are well known to those skilled in the art and include, but are not limited to, administering the compositions orally, parenterally (e.g., intravenously and subcutaneously), by intramuscular or intraperitoneal injection, intrathecally, transdermally, extracorporeally, topically or the like.

In some embodiments, a composition comprising the opioid receptor antagonist, e.g. KPR antagonist, can also be administered by topical intranasal administration (intranasally) or administration by inhalant. As used herein, "topical intranasal administration" means delivery of the compositions into the nose and nasal passages through one or both of the nares and can comprise delivery by a spraying mechanism (device) or droplet mechanism (device), or through aerosolization of the composition. Administration of the compositions by inhalant can be through the nose or mouth via delivery by a spraying or droplet mechanism. As used herein, "an inhaler" can be a spraying device or a droplet device for delivering a composition comprising the KOR antagonist, in a pharmaceutically acceptable carrier, to the nasal passages and the upper and/or lower respiratory tracts of a subject. Delivery can also be directly to any area of the respiratory system (e.g., lungs) via intratracheal intubation. The exact amount of the compositions required will vary from subject to subject, depending on the species, age, weight and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation given the teachings herein.

In other embodiments, the composition comprising the opioid receptor antagonist can also be administered by buccal delivery or by sublingual delivery. As used herein "buccal delivery" may refer to a method of administration in which the compound is delivered through the mucosal membranes lining the cheeks. In some embodiments, for a buccal delivery the KOR antagonist is placed between the gum and the cheek of a patient. As used herein "sublingual delivery" may refer to a method of administration in which the compound is delivered through the mucosal membrane under the tongue. In some embodiments, for a sublingual delivery the KOR antagonist is administered under the tongue of a patient.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, for example, U.S. Pat. No. 3,610,795, which is incorporated by reference herein.

A "therapeutically effective amount" refers to an amount that is sufficient to achieve the desired therapeutic result or to have an effect on undesired symptoms but is generally insufficient to cause intolerable adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of the composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

As described above, the compositions can be administered to a subject in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Typically, an appropriate amount of a pharmaceutically acceptable salt is used in the formulation to render the formulation isotonic. Examples of the pharmaceutically acceptable carrier include, but are not limited to, saline, Ringer's solution and dextrose solution. The pH of the solution is preferably from about 5 to about 8, and more preferably from about 7 to about 7.5. Further carriers include sustained release preparations such as semi-permeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. A preferred mode of administration of the composition is orally. Other modes of administration may be topically (including ophthalmically, vaginally, rectally, intranasally), by inhalation, or parenterally, for example by intravenous drip, subcutaneous, intraperitoneal or intramuscular injection. The disclosed compounds can be administered orally, intravenously, intraperitoneally, intramuscularly, subcutaneously, intracavity, transdermally, sublingually or through buccal delivery.

Pharmaceutical compositions for oral administration include, but are not limited to, powders or granules, suspensions or solutions in water or non-aqueous media, capsules, sachets, or tablets. Thickeners, flavorings, diluents, emulsifiers, dispersing aids or binders may be desirable. The composition of the KOR antagonist can be administered to a subject orally in a dosage taken once daily or in divided doses. A person of skill, monitoring a subject's clinical response, can adjust the frequency of administration of the medication according to methods known in the art.

Preparations for parenteral administration include sterile aqueous or non-aqueous solutions, suspensions, and emulsions. Examples of non-aqueous solvents are propylene glycol, polyethylene glycol, vegetable oils such as olive oil, fish oils, and injectable organic-esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like may be necessary or desirable.

In one aspect, the KOR antagonist can be administered in an intravenous dosage. This dosage can be administered to a subject once daily or in divided doses throughout a day, as determined by methods known in the art. This dosage can be administered to a subject on a daily basis until a clinical response is noted. It is contemplated that the dosage of the KOR antagonist can be administered as infrequently as once daily or weekly, or at any interval in between, depending on a subject's clinical response to the medication. If a subject does not respond to the initial dosage and administration of the KOR antagonist, a person of skill can administer the medication daily for several days until such response occurs. A person of skill can monitor a subject's clinical response to the administration of the KOR antagonist and administer additional dosages if the subjects sleep disruption symptoms reappear after a period of remission. It is contemplated that the KOR antagonist can be administered to a subject with, for example, a sleeping problem due to chronic pain on a twice daily basis, once daily basis, on an alternating daily basis, on a weekly basis, on a monthly basis, or at any interval in between.

In another aspect, the KOR antagonist can be administered to a subject transdermally, by using an adherent patch, by using iontophoresis, or by using any other method known to a person of skill. The dosage of the KOR antagonist, administered transdermally can be given daily or weekly, or at any interval in between. A person of skill, monitoring a subject's clinical response and improvement, can determine the frequency of administration of the medication by methods known in the art.

In another aspect, the KOR antagonist can be administered to a subject intranasally in a dosage taken once daily or in divided doses. The medication can be administered daily or weekly, or at any interval in between. A person of skill, monitoring a subject's clinical response to the administration of the medication, can adjust the frequency of administration according to methods known in the art.

In another aspect, the KOR antagonist can be administered to a subject intramuscularly in a dosage taken once daily or in divided doses. The medication can be administered daily or weekly, or at any interval in between. A person of skill, monitoring a subjects clinical response, can adjust the frequency of administration of the medication according to methods known in the art.

In some embodiments, the present invention uses an antagonist of the kappa opioid receptor signaling pathway to help improve total sleep time, increase non-REM sleep, and reduce fragmented sleep due to chronic pain. Additionally, the antagonist helps to reduce daytime sleepiness. In some embodiment, the present invention may be used in combination with other treatments.

The present invention is not limited to treatment of sleep disturbance induced by chronic pain but can also be applied to other conditions where the kappa opioid receptor (KOR) signaling pathway is induced promoting sleep disturbances. In some embodiment these conditions include, but are not limited to, depression, generalized anxiety disorder, alcoholism or drug addiction. In other embodiments, sleep disturbances may induce KOR signaling.

In some embodiments, chronic pain may induce sleep disturbance. In other embodiments, sleep disturbance may induce chronic pain. In further embodiments, chronic pain and sleep disturbance are reciprocal and may induce a positive feedback loop.

In some embodiments, the treatment of age-related sleep disruption with a KOR antagonist normalizes sleep in a subject. In other embodiments, the treatment of age-related sleep disruption with a KOR antagonist prevents cognitive impairment in a subject. In further embodiments, the treatment of age-related sleep disruption with a KOR antagonist produces natural sleep in a subject. In some embodiments, the treatment of age-related sleep disruption with a KOR antagonist normalizes sleep, prevents cognitive impairment, normalized sleep or a combination thereof in a subject.

EXAMPLES

The following are non-limiting examples of the present invention. It is to be understood that said examples are not intended to limit the present invention in any way. Equivalents or substitutes are within the scope of the present invention.

Figures 2A, 2B, 2C:
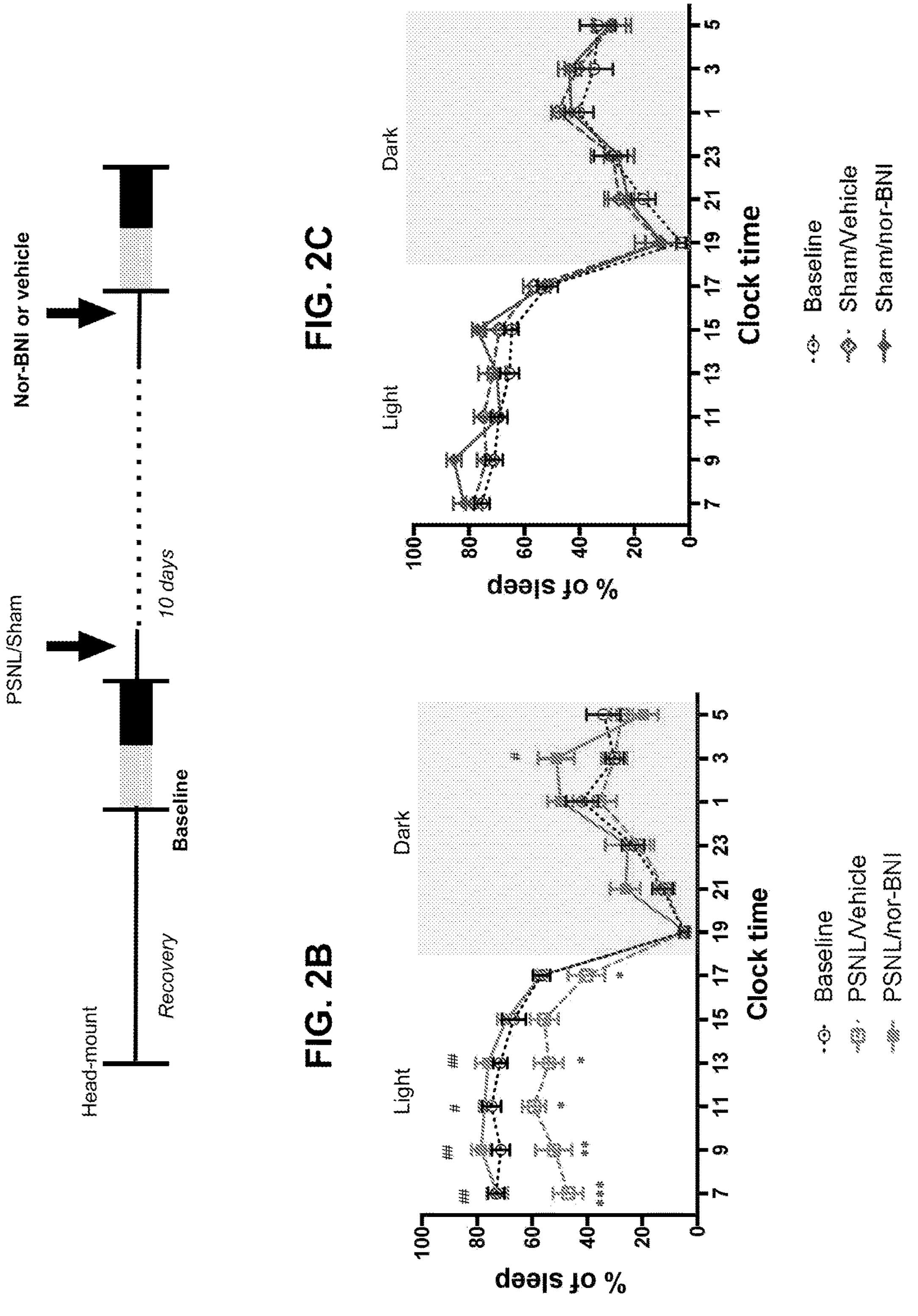

Example 1: Describes how a Kappa Opioid Receptor Antagonist Improves Sleep Conditions in a Preclinical Model of Chronic Pain Norbinaltorphimine (nor-BNI) was dissolved in 0.9% saline to 10 mg/kg just before injection. C57BL/6J mice received intraperitoneal injection of nor-BNI or vehicle (0.9% saline) 30 minutes before EEG/EMG record at 10 days after partial sciatic nerve ligation (PSNL) surgery (FIG. 2A). CYM-53093 was synthesized as described previously by Guerrero et al. It was dissolved in DMSO, tween and saline at a ratio of 1:1:8. C57BL/6J mice were implanted with a micro-osmotic pump under the skin at 8 days after PSNL surgery and received continuous infusion of CYM-53093 (10 mg/kg/day) or vehicle. Mice had surgical recovery for 1 day after pump implantation followed by EEG/EMG record for 5 days (FIG. 3A).

EEG/EMG recording head-mount implantation was done under 2-5% isoflurane anesthesia, mice were implanted with EEG and EMG electrodes for polysomnographic recordings (Pinnacle Technology, Oregon, USA) as described previously by Ito et al. Recording was done in awake animals after acclimatization using EEG/EMG mouse sleep equipment from Pinnacle Technology. The collected EEG/EMG data were analyzed by software (Sleepsign; Kissei Comtec, Japan). The vigilance of every 5-second epoch was automatically classified into three stages, i.e., wakefulness, REM and non-REM sleep, according to the standard criteria. As a final step, defined sleep-wake stages were examined visually and corrected, if necessary. The vigilance states were assessed as follows: 1) wakefulness was defined by a high EMG amplitude, low EEG amplitude; 2) REM sleep was defined by a low EMG amplitude, low EEG amplitude, and high 0 wave (5.0-10.0 Hz) activity; and 3) non-REM sleep was defined by a low EMG amplitude, high EEG amplitude, and high 8 wave (0.65-4.5 Hz) activity.

Figures 2D, 2E, 2F, 2G, 2H:
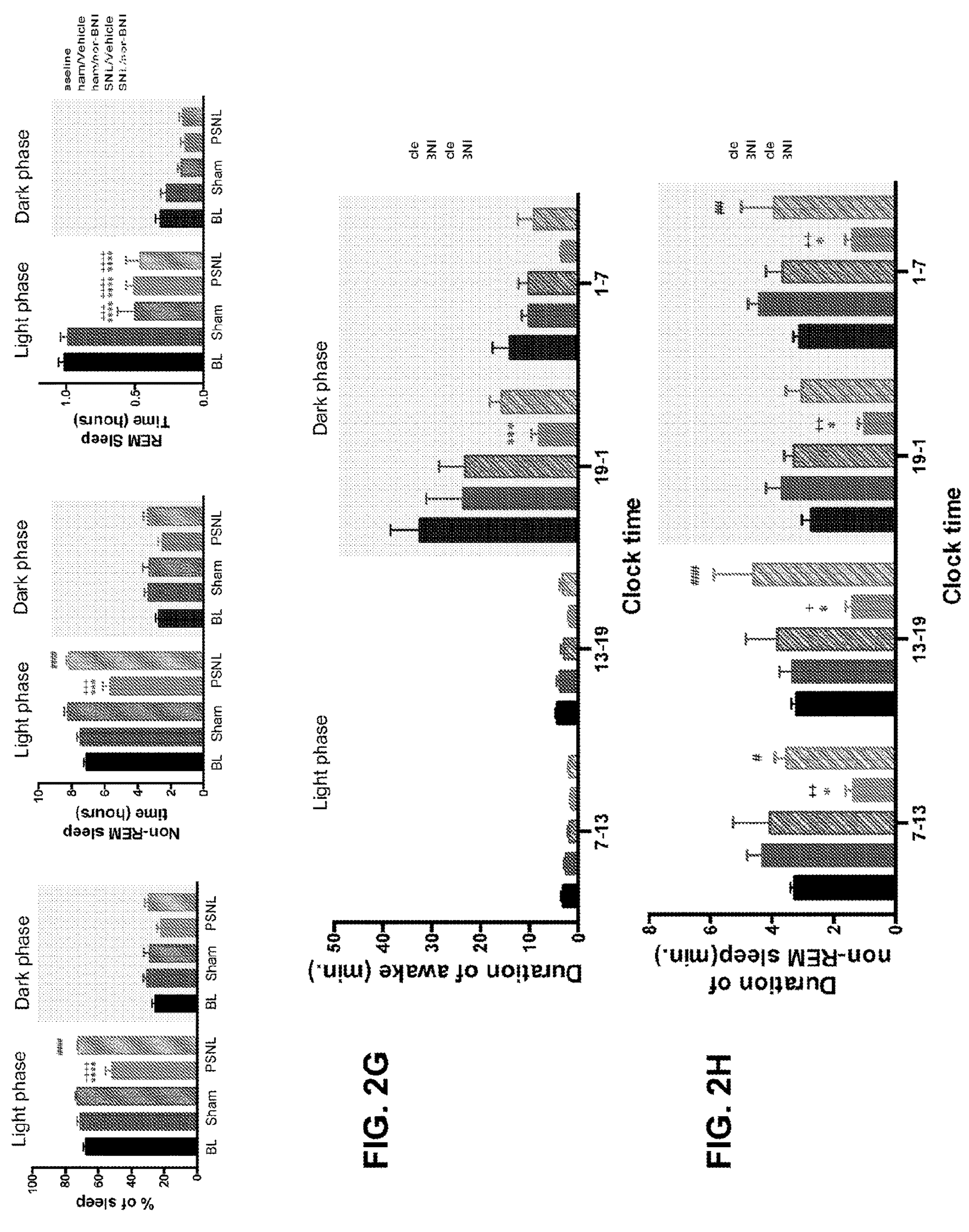
Figure 6:
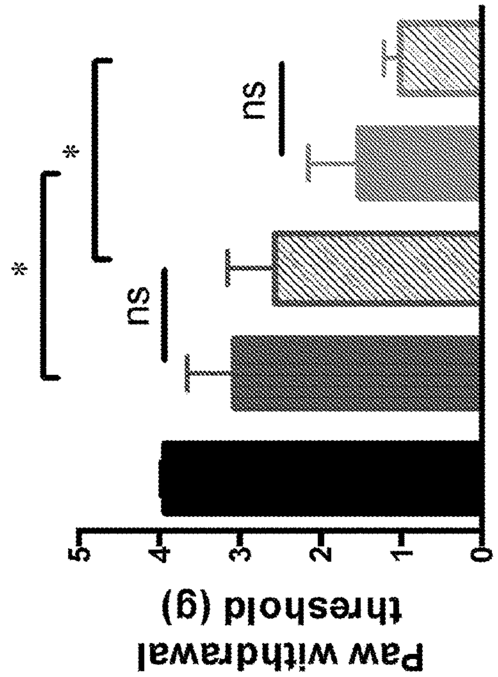
FIG. 6 shows KOR antagonist (nor-BNI) did not alter mechanical allodynia in naïve or injured animals, suggesting that nor-BNI does not have any effects on pain, but normalizes pain-induced sleep disruption.
Figure 7:
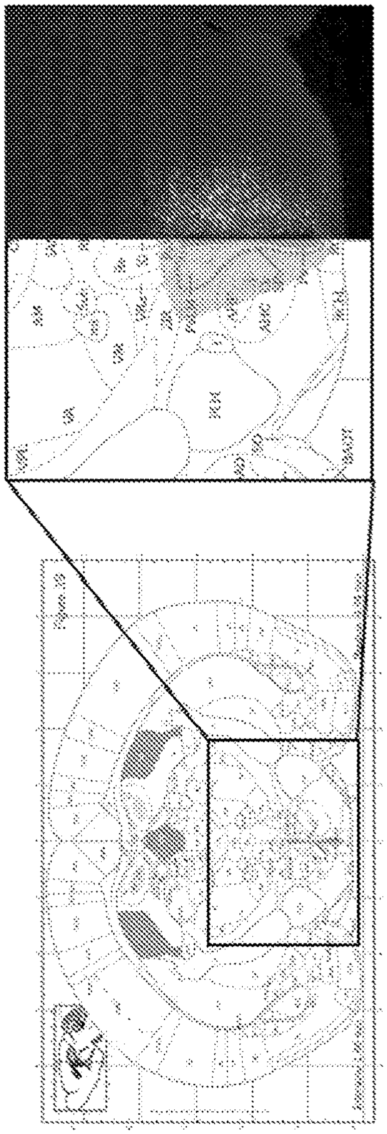
FIG. 7 shows the expression of hM4Di and mCherry was verified in the hypothalamus (control for the experiment in FIG. 4).
Figure 8:
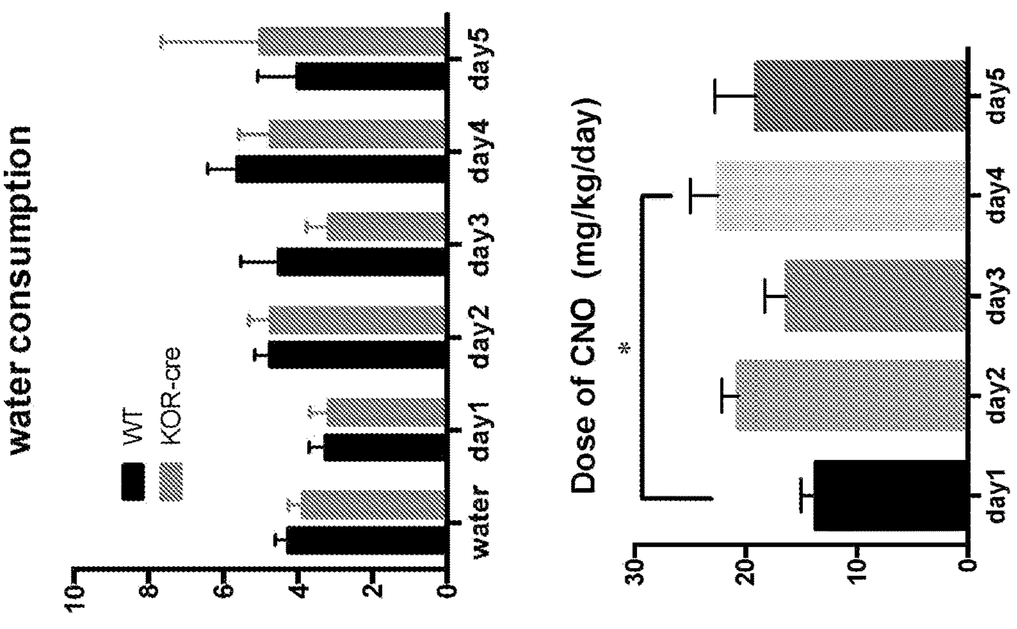
FIG. 8 shows there are no differences in water consumption between wild type and KOR-cre mice.
Figure 9:
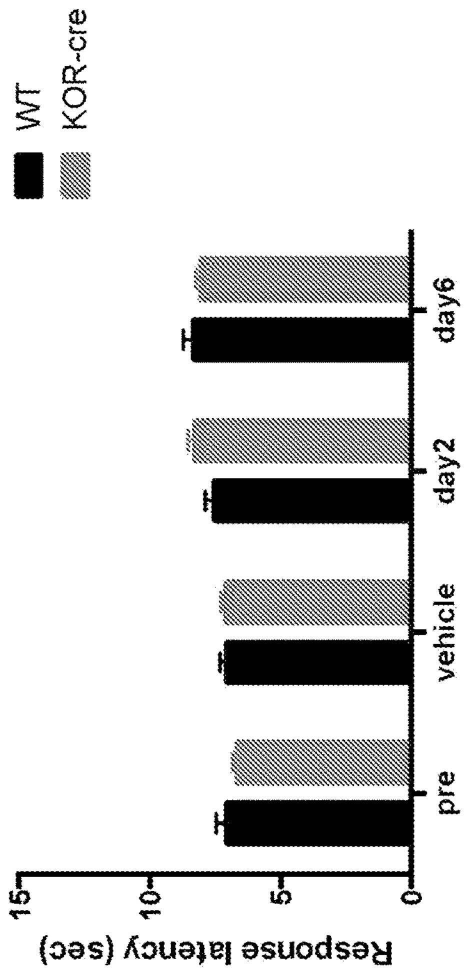
FIG. 9 shows there are no differences in pain sensitivity between wild type and KOR-cre mice.

To investigate the effect of the long acting KOR antagonist, nor-BNI, on sleep disruption in preclinical model of chronic pain, the percentage of sleep time for 24 hours between the groups administered nor-BNI or vehicle 10 days after partial sciatic nerve ligation (PSNL), and baseline before PSNL surgery were compared (FIG. 2A). The sham groups were also evaluated in the same time series as PSNL groups. It was confirmed with von Frey test that PSNL reduced the paw withdrawal threshold (i.e., produced tactile allodynia), and nor-BNI did not influence the evoked allodynia demonstrating no effect on sensory qualities of pain (FIG. 6). First, in order to evaluate the sleep-wake cycle of each group, the changes in the percentage of sleep time were examined every two hours. PSNL/vehicle group significantly decreased sleep time compared with baseline during the light phase. Administration of nor-BNI (10 mg/kg, i.p.) normalized the reduction of sleep time of the PSNL group almost to the same level as baseline (FIG. 2B). Sham surgery and administration of nor-BNI to sham groups had no significant effect on sleep time (FIG. 2C). Secondly, the percentage of total sleep (FIG. 2D), non-REM sleep (FIG. 2E), and REM sleep (FIG. 2F) were evaluated and time in the light phase and dark phase were evaluated separately. The percentage of total sleep in PSNL/vehicle group (46.1±2.6%) was significantly lower than at baseline (69.2±1.1%; $P<0.0001$) and sham/vehicle group (69.9±3.1%; $P<0.0001$) during light phase. Administration of nor-BNI normalized the percentage of sleep time of PSNL group (71.4±1.3%) to the same level as baseline and sham (FIG. 2C). PSNL reduced both non-REM and REM sleep time significantly. Although administration of nor-BNI increased non-REM sleep time, it did not improve REM sleep time (FIGS. 2E and 2F). In sham animals, there was no significant difference in the percentage of total sleep and non-REM sleep between nor-BNI treated and vehicle treated groups (FIGS. 2D and 2E). However, nor-BNI significantly reduced REM sleep time in sham mice (FIG. 2F). Then, duration of awake and non-REM sleep was evaluated at 6-hour intervals (early and late light phase and early and late dark phase), and compared between baseline, sham/vehicle group, PSNL/vehicle group, sham/nor-BNI group, and PSNL/nor-BNI group. At baseline, mice showed sustained long-term arousal during the early half of the dark phase, but this persistence of wakefulness in PSNL/vehicle group was significantly shortened. Although nor-BNI tended to extend this duration somewhat, it was not significant (FIG. 2G). The duration of non-REM sleep in the PSNL/vehicle group was significantly shorter than at baseline and in the sham/vehicle group at all time intervals (FIG. 2H). Nor-BNI improved this fragmented sleep by PSNL (FIG. 2H). Power spectrum during non-REM sleep was unchanged in both groups (FIG. 2I).

Figures 2I, 3A, 3B:
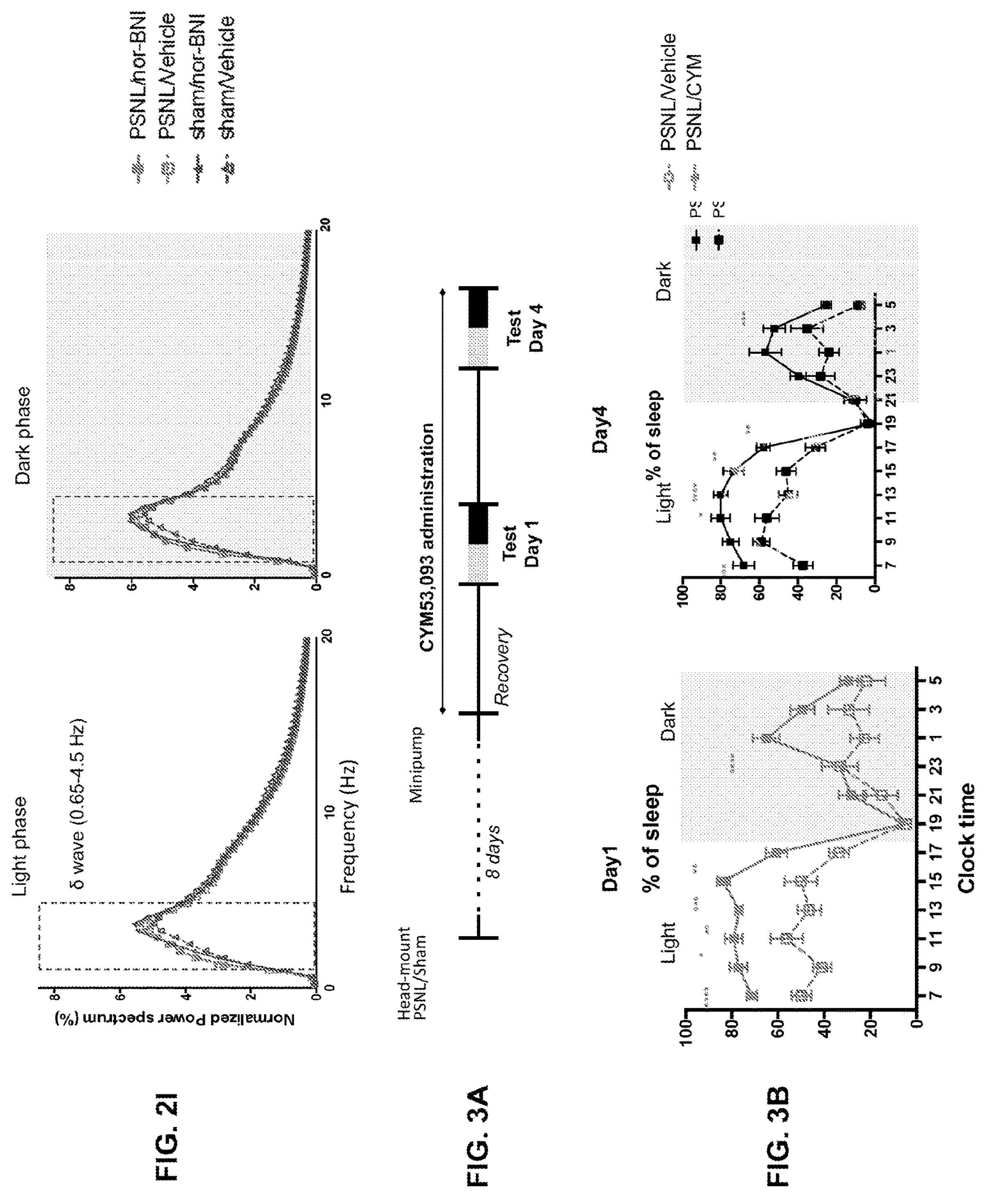
Figures 3C, 3D, 3E, 3F:
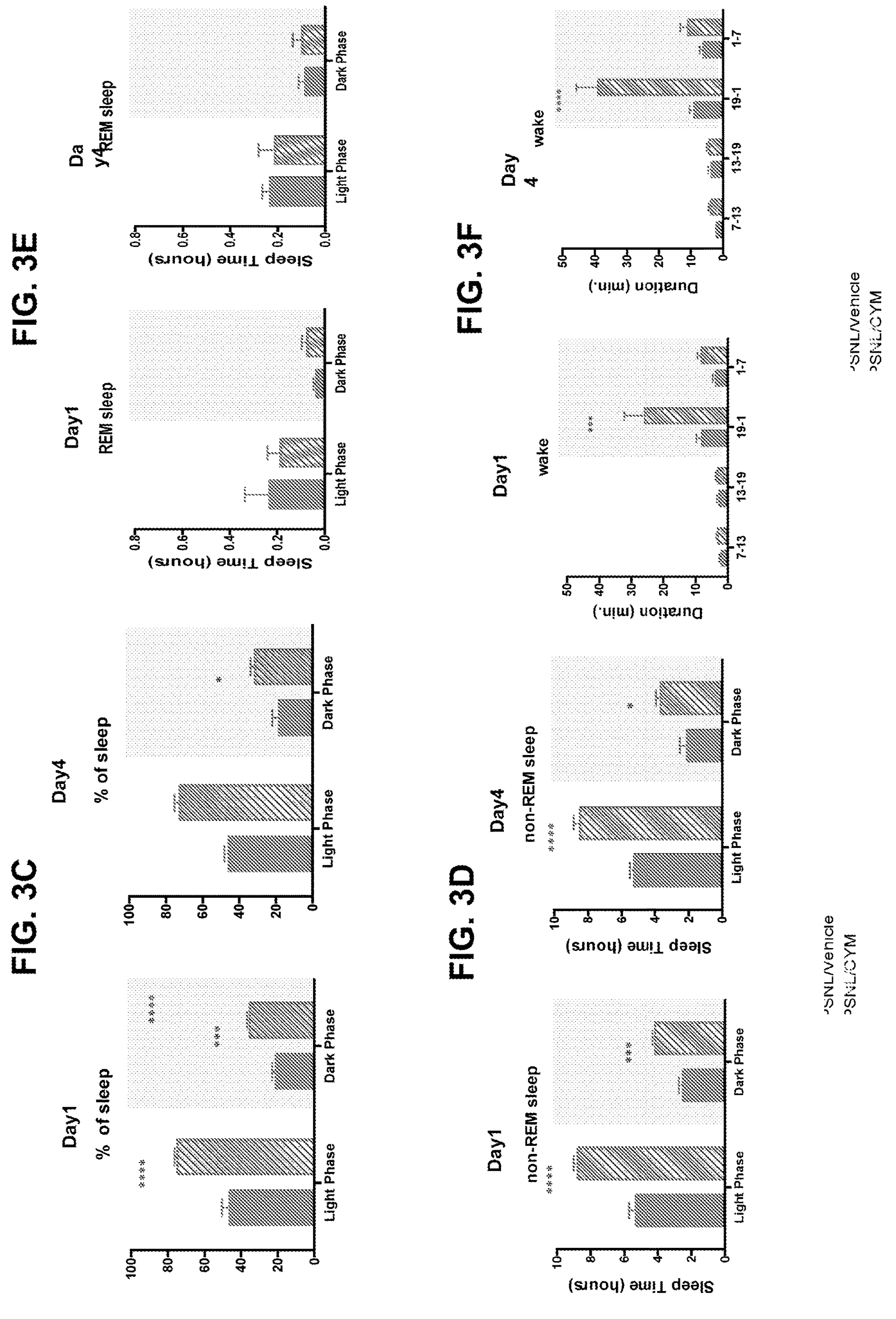
Figures 3G, 3H, 4A:
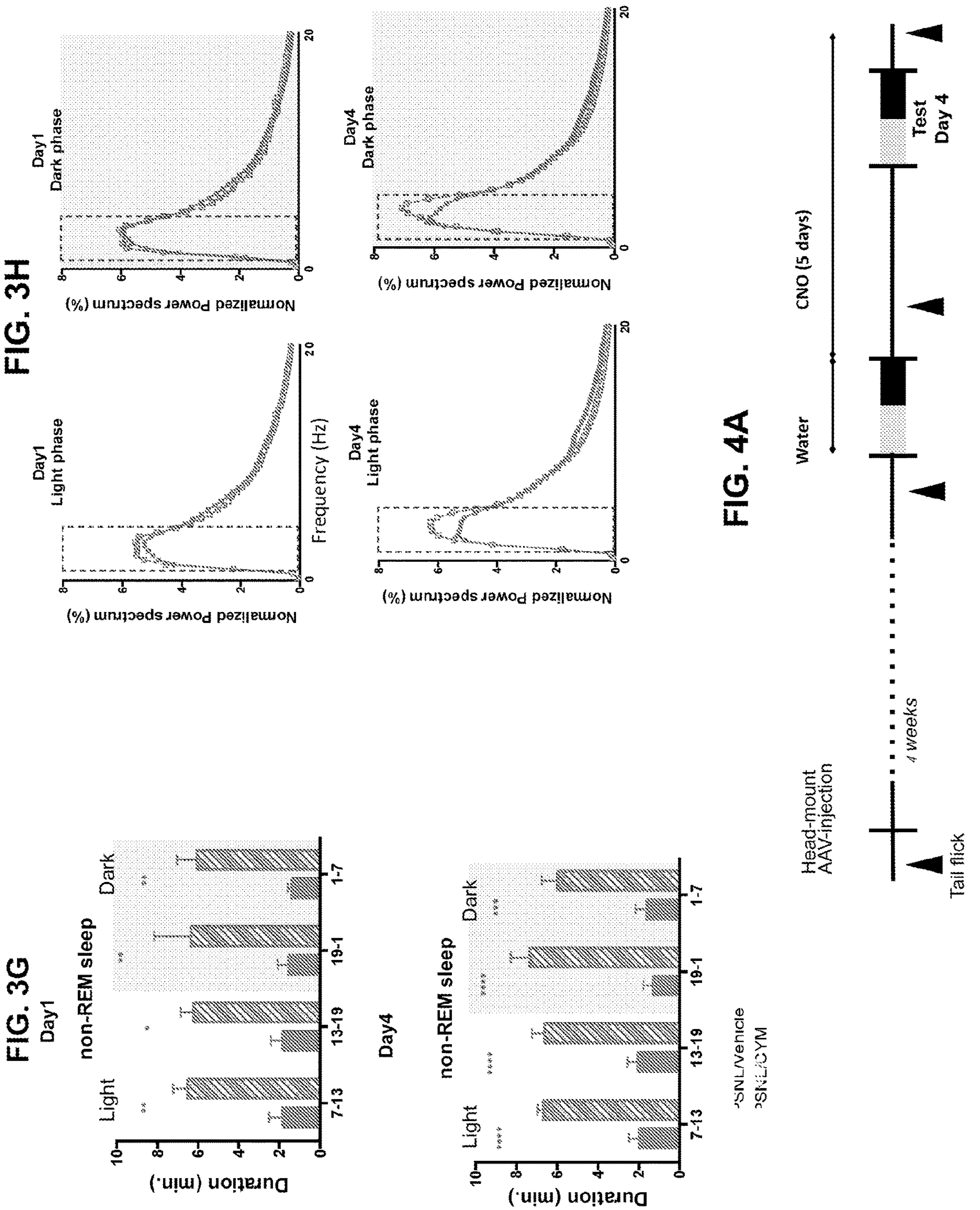
Figure 4B:
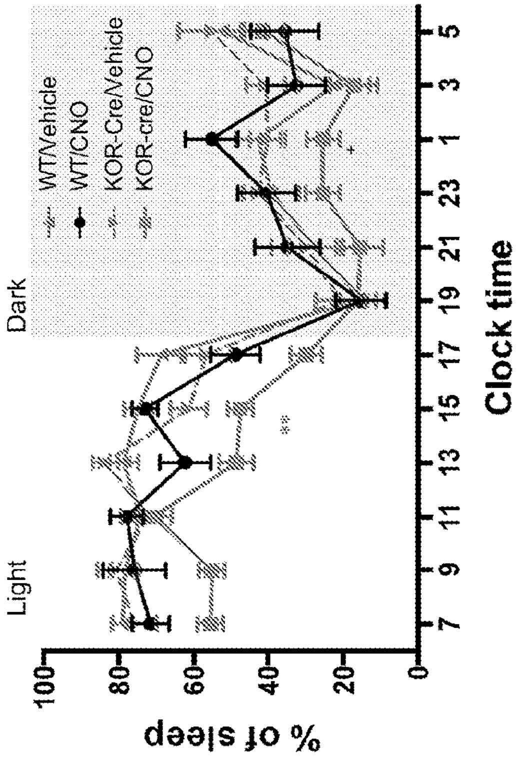
Figure 4C:
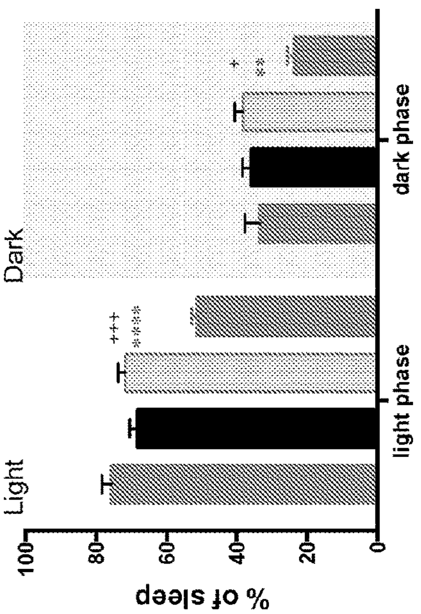
Figure 4C:
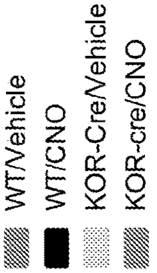
Figure 4D:
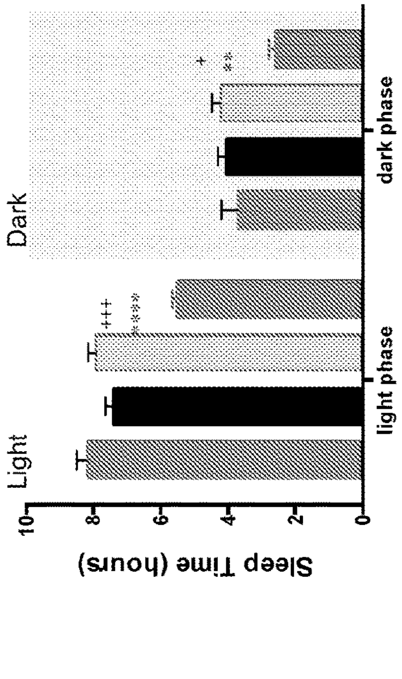
Figure 4E:
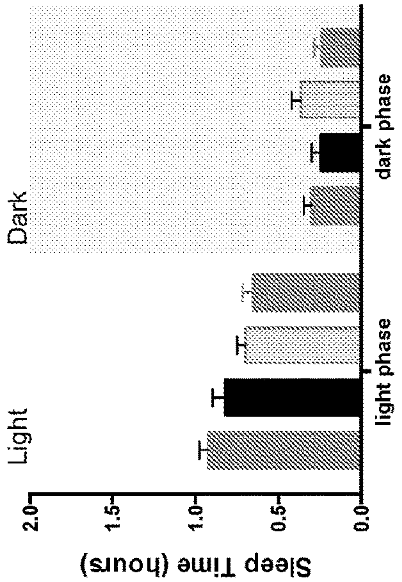
Figure 4H:
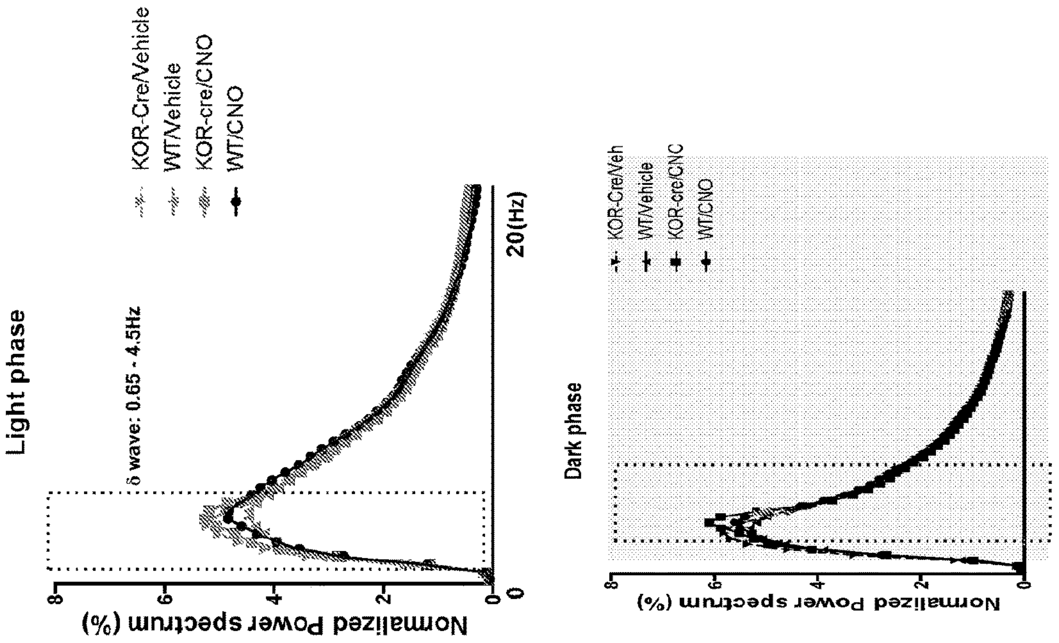
Figure 4F:
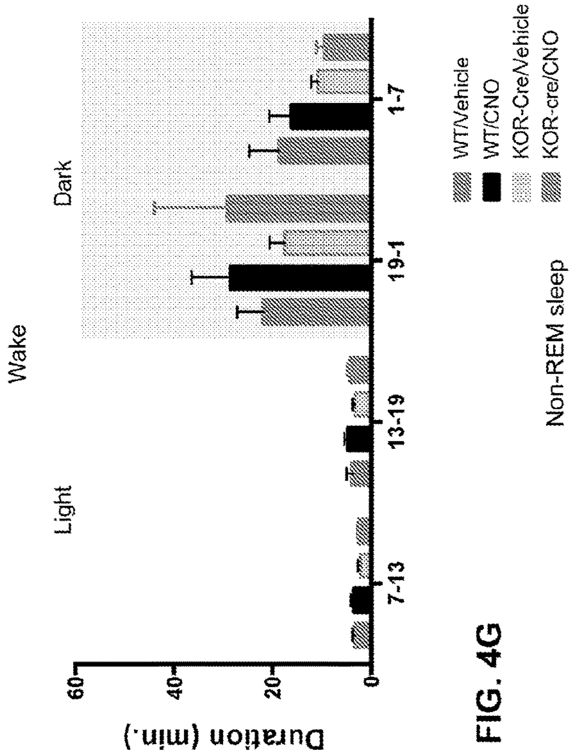
Figure 4G:
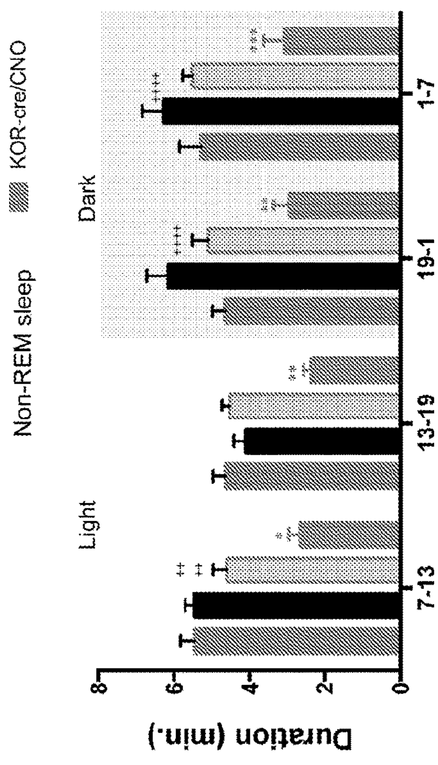
Figure 5:
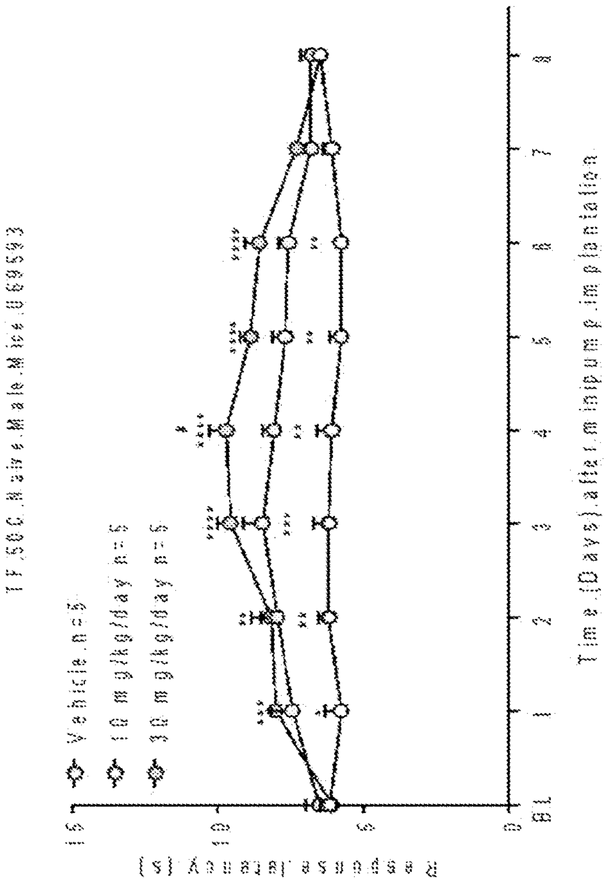
FIG. 5 shows continuous KOR agonist (U69,593) administration induced antinociception, demonstrating that the same U69.593 dosage regiment used in FIG. 1A was effective in engaging KOR receptors. Note that the peripheral and spinal effects of KOR agonists suggest pain relief, while, surprisingly, the same dosage promotes sleep disruption similar to sleep disruption observed in PSNL animals.

A KOR antagonist with a half-life of approximately 24-36 hours was tested to evaluate the effects of continuous administration on sleep in the chronic pain model (FIG. 3A). As same as nor-BNI, CYM53093 normalized the reduction of sleep time and the effect lasted at least until day 4 (FIGS. 3B and C). CYM53093 mainly influenced non-REM sleep, but not REM sleep (FIGS. 3D and E). CYM53093 also improved short duration of wakefulness at the first half of the dark phase (FIG. 3F). CYM53093 normalized fragmentation of non-REM sleep (FIG. 3G). PSNL model shows an increase in the power density of δ wave during non-REM sleep at test day 4, however the power density of CYM group did not change (FIG. 3H).

Example 2: Describes how a Kappa Opioid Receptor Antagonist can Improve Age-Related Sleep Disturbances Animals: Both male or female mice (24 months old) will be used for all experiments. Mice will be maintained under conditions with a 12-hour light-dark cycle. Clock time 7 and 19 o'clock represent light onset and offset times, respectively. Food and water are available ad libitum.

EEG/EMG recording: Under 2-5% isoflurane anesthesia, mice will be implanted with EEG and EMG electrodes for polysomnographic recordings (Pinnacle Technology, Oregon, USA). Mice will be mounted in a stereotaxic head holder. Approximately 2 cm incision is made down the midline from just behind the eyes to the ear to expose the cranium. Four holes are positioned 1 mm anterior to the bregma or lambda, both 1.5 mm lateral to the midline and drilled avoiding visible blood vessels to allow for implantation of electrode screws into each of the holes. Dedicated 2 EEG/1 EMG mouse head-mount (Pinnacle Technology. Oregon, USA) are implanted with four EEG electrode screws. Two teflon-coated stainless steel wires are placed bilaterally into both trapezius muscles to record EMG. The dental acrylic covered the entire opening, sealing the wound.

Sleep analysis: The collected EEG/EMG data will be analyzed by software (Sleepsign; Kissei Comtec, Japan). The vigilance of every 5-second epoch is automatically classified into three stages, i.e., wakefulness, REM and non-REM sleep, according to the standard criteria. As a final step, defined sleep-wake stages will be examined visually and corrected, if necessary. The vigilance states that are assessed include: 1) wakefulness defined by a high EMG amplitude, low EEG amplitude; 2) REM sleep defined by a low EMG amplitude, low EEG amplitude, and high 0 wave (5.0-10.0 Hz) activity; and 3) non-REM sleep defined by a low EMG amplitude, high EEG amplitude, and high 6 wave (0.65-4.5 Hz) activity. This analysis will allow for assessment of the following outcome measures: Onset insomnia, decreased total sleep time, REM sleep periods, daytime sleepiness, fragmented sleep and disruption of deep sleep.

Example 3 Describes Treatment of Secondary Sleep Disturbance Induced by Chronic Pain Involving Oral Administration of a KOR Antagonist A 64-year-old patient with type 2 diabetes mellitus makes an appointment with her primary care physician. During her appointment, she brings up that she has been having trouble managing her blood sugar, and finds it tends to be too high. She also notes that she has begun to feel a tingling in her feet. After some testing her doctor diagnoses her with peripheral neuropathy. The patient returns to the doctor, the tingling in her feet has now become painful, with the pain increasing during the night. The excessive pain she experiences during the night is keeping her awake. The doctor prescribes her a pill comprising 20 mg of a KOR antagonist to be taken orally once a day before bed, to help decrease her pain and help her sleep. After a month of taking the KOR antagonist, the patient's symptoms improve, and she informs her doctor that she is able to sleep through the night. No side effects are reported.

Example 4 Describes Treatment of Secondary Sleep Disturbance Induced by Chronic Pain Due to Migraines Involving Oral Administration of a KOR Antagonist A 32-year-old patient makes an appointment with her primary care physician. For months, she has been having painful migraines that have been limiting her work and use of an over the counter pain medication have only been slightly helpful. Her primary care physician refers her to a neurologist to look further into the situation. She describes to the neurologist, that she has throbbing pain on the left side of her head, becomes sensitive to light, and slightly nauseous during the episodes. The neurologist asks the patient to write down each episode in a journal for three months. After three months the patient returns, after reviewing the patients journal the neurologist determines the patient has chronic migraines, having migraines more than 15 days each month. The neurologist puts her on a restrictive diet to try and reduce the migraine severity. However, after a couple of months the patient still finds no relief. The neurologist prescribes her a pill comprising 10 mg of a KOR antagonist to be taken orally once a day before bed, to help decrease the frequency of her migraines. After a month of taking the KOR antagonist, the patient's symptoms improve, and she informs her doctor that she has almost no migraines and her sleep has now returned to normal. No side effects are reported.

Example 5 Describes Treatment of Secondary Sleep Disturbance Induced by Chronic Pain Due to Fibromyalgia Involving Oral Administration of a KOR Antagonist After years of having chronic muscle pain and fatigue a 45-year-old woman has recently been diagnosed with fibromyalgia. Her doctor prescribes her medication to help her deal with the pain associated with the disease. After taking the medication for a couple of months, the woman does notice a slight decrease in pain. However, she is increasingly finding it harder to sleep through the night and is feeling more tired throughout the day. She makes another appointment with her doctor to discuss possible alternatives to her current medication. The doctor prescribes her 40 mg of a KOR antagonist to be taken twice a day. After two weeks the woman reports that she is sleeping better at night and is less sleepy during the day. Additionally, she notes that her pain levels have gone down dramatically. No side effects are reported.

Example 6 Describes Treatment of Secondary Sleep Disturbance Induced by Chronic Pain Due to Irritable Bowel Syndrome (IBS) Involving Oral Administration of a KOR Antagonist For over five years a 38-year-old man has been successfully living with IBS. He has been able to manage his symptoms through dietary changes, regular exercise, and taking a probiotic daily. However, recently the man's symptoms have gotten worse. He makes an appointment with his gastroenterologist (GI) doctor to discuss the recent developments with his health. During his appointment the man tells the doctor that his most severe symptom is frequent bouts of abdominal pain that happen at all hours. During the night the abdominal pain can be so severe that it wakes him up from his sleep and he is unable to fall back asleep. The doctor tells the man to continue with his routine but prescribes the man 100 mg of a KOR antagonist to be taken orally twice a day. After a week of treatment, the man's abdominal pain subsides, and he is able to sleep fully through the night. No side effects are reported.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or consisting of is met.

What is claimed is:

1. A method of treating a secondary sleep disturbance induced by chronic pain in a subject in need of such treatment, said method comprising administering a therapeutic amount of an opioid receptor antagonist comprising CYM 53,093, thereby simultaneously treating both the secondary sleep disturbance and the chronic pain.

2. The method of claim 1, wherein the opioid receptor antagonist is specific for a kappa opioid receptor.

3. The method of claim 1, wherein the opioid receptor antagonist is used for an extended period of time, wherein an extended period of time ranges from a week to a year or more.

4. The method of claim 1, wherein the opioid receptor antagonist is given at a dose of about 0.1 mg to about 1000 mg.

5. The method of claim 1, wherein the opioid receptor antagonist is used in combination with other treatments.

6. A method of treating an age-related sleep disturbance in a subject in need of such treatment, said method comprising administering a therapeutic amount of an opioid receptor antagonist comprising CYM 53,093.

7. The method of claim 6, wherein the opioid receptor antagonist is specific for a kappa opioid receptor.

8. The method of claim 6, wherein the opioid receptor antagonist is used for an extended period of time, wherein an extended period of time ranges from a week to a year or more.

9. The method of claim 6, wherein the opioid receptor antagonist is given at a dose of about 0.1 mg to about 1000 mg.

10. The method of claim 6, wherein the opioid receptor antagonist is used in combination with other treatments.

* * * * *